United States Patent [19]

Seal

[11] Patent Number: 4,857,065
[45] Date of Patent: Aug. 15, 1989

[54] ABSORBENT PRODUCTS
[75] Inventor: Michael J. Seal, Dunblane, Scotland
[73] Assignee: Bonar Carelle Limited, Dundee, Scotland
[21] Appl. No.: 122,357
[22] Filed: Aug. 15, 1989
[30] Foreign Application Priority Data
Nov. 21, 1986 [GB] United Kingdom ............... 8627916
[51] Int. Cl.$^4$ ............................................. A61F 13/16
[52] U.S. Cl. .................................. 604/368; 428/213;
428/218; 428/219; 428/280; 428/281; 428/282;
428/283; 428/284; 428/287; 428/296; 428/298;
428/402; 428/913
[58] Field of Search ............... 428/219, 283, 218, 213,
428/284, 298, 402, 913, 296, 287, 280, 281, 282;
604/368, 378

[56] References Cited
U.S. PATENT DOCUMENTS
4,377,615 3/1983 Suzuki et al. ....................... 428/218

Primary Examiner—James J. Bell
Attorney, Agent, or Firm—Lyon & Lyon

[57] ABSTRACT

An absorbent product, for example a diaper, comprises an absorbent member (3), for example a pad formed of comminuted cellulose fibres or a superabsorbent polymer, and a particle-bonded nonwoven material (1) having an outer phase (4) that is in an unlofted state and an inner phase (5) that is in a lofted state. The nonwoven may be formed of polyester fibres bonded with a polyester adhesive. The product may also comprise a liquid-impermeable backing sheet (2).

11 Claims, 2 Drawing Sheets

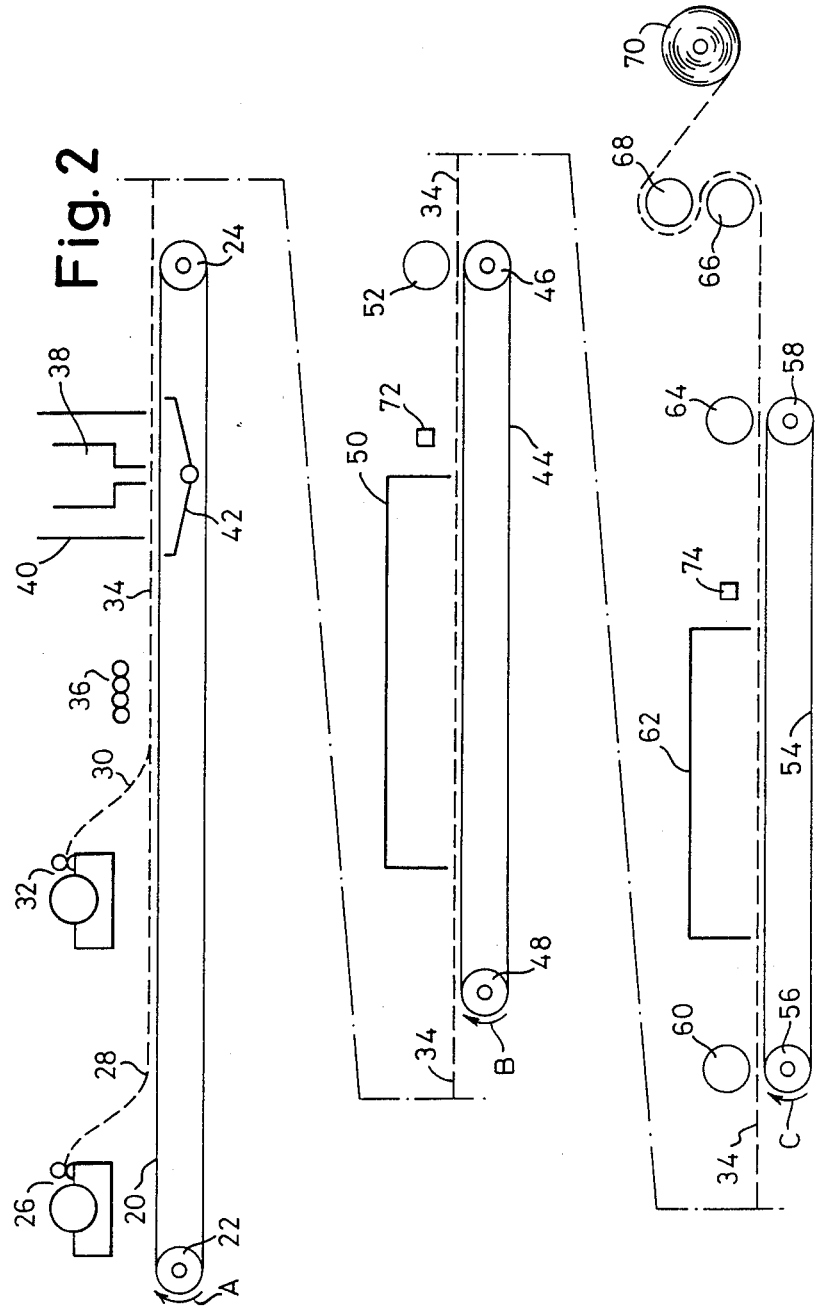

ABSORBENT PRODUCTS

FIELD OF THE INVENTION

The present invention relates to absorbent products, especially such products that are used for the purposes of personal hygiene to collect liquids such as urine and blood exuded from the human body. Such products include those which may be broadly described as "diapers", for example babies' napkins, incontinence pads for adult use and ladies' sanitary towels.

BACKGROUND OF THE INVENTION

Conventionally, absorbent products for personal use comprise a core of absorbent material which is provided with a liquid-impermeable backing intended to prevent loss of the absorbed liquid and thereby prevent contamination of clothing, bed sheets and the like. The surface of the absorbent product that in use is in contact with the wearer is formed of "coverstock", this being a liquid-permeable sheet material having a relatively smooth surface in order to minimise discomfort to the wearer. Suitable coverstock materials include thermobonded nonwovens, although spunbonded nonwovens and perforated films have also been proposed for this purpose.

It is also known to interpose between the coverstock and the absorbent core a discrete layer of hydrophobic material which draws liquid towards the absorbent core, thereby keeping the coverstock relatively dry and so improving comfort and reducing the likelihood of skin rashes. A hydrophobic layer of this type may be referred to as a "dry bridge", since it reduces the re-wetting of the coverstock with moisture from the absorbent core.

Although the coverstock does not contribute to the absorption characteristics of these products, its use has so far been considered essential, in order to achieve consumer acceptance.

SUMMARY OF THE INVENTION

It has now been found that coverstock may be eliminated from absorbent products whilst maintaining adequate comfort characteristics for the wearer. In particular, the present invention provides an absorbent product comprising an absorbent member at least part of which is overlaid with a sheet of particle-bonded (e.g. powder-bonded) nonwoven material having a first phase that is in an unlofted state and a second phase that is in a lofted state, the said second phase being between the said first phase and the absorbent member.

BRIEF DESCRIPTION OF THE DRAWINGS

FIG. 2 is a flow-sheet showing various stages in the manufacture of a two-phase powder-bonded nonwoven suitable for use in this invention.

DESCRIPTION OF PREFERRED EMBODIMENTS

Figure 1:
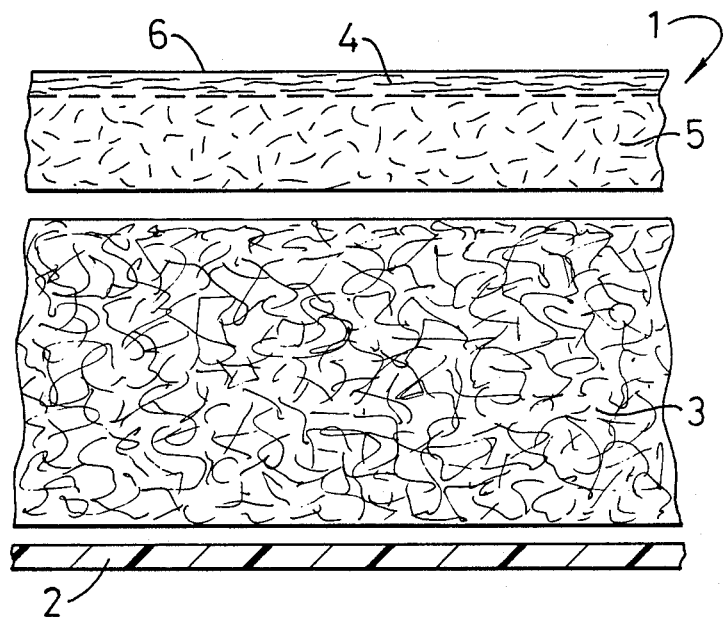
FIG. 1 is a diagrammatic cross-section through an absorbent product of this invention, showing the component layers therein.

An absorbent product of this invention comprises a particle-bonded nonwoven having first and second phases, as defined above; the use of nonwovens having one or more additional phases, although not currently preferred, is not precluded. The fibres in each phase may be selected, independently of the other phase(s), from natural fibres (e.g. cotton linters), regenerated fibres (e.g. viscose rayon) and synthetic polymers (e.g. polyesters, such as poly(ethylene terephthalate), polyamides such as nylon 6 or nylon 6,6, and polyalkylenes such as polypropylene), as well as any mixtures of two or more such fibres. However, it is preferred to use polyester fibres in both the first and the second phase.

The fibres will have a staple length usually of from 25 to 100 mm, preferably from 35 to 60 mm, and a linear density usually of from 0.5 to 20 dtex, preferably from 1.5 to 15 dtex.

The first phase will usually have a basis weight ("grammage") of from 10 to 50 $g/m^2$, preferably 15 to 25 $g/m^2$, whereas the second phase will usually have a basis weight of from 30 to 80 $g/m^2$, preferably from 50 to 60 $g/m^2$.

The absorbent member may be composed of a material that is conventionally used in absorbent products such as diapers. Thus, for example, the member may be formed as a batt of comminuted cellulose fibres ("cellulose fluff"). However, other materials come into consideration, for example hydrophilic polymers, especially the so-called "superabsorbent" polymers, particles of which may be distributed in or on a suitable substrate or matrix, for instance of a suitable fibrous material, e.g. cellulose fluff or a nonwoven web. Particulate superabsorbent polymers are commercially available (e.g. under the Trade Mark "Aqua Keep" from Norsolor, France), as are various types of equipment for applying them to appropriate carrier materials (e.g. the powder-spray equipment from Nordson Corporation, Ohio, U.S.A.; the apparatus utilising a dosing roller available from Santex AG, Tobel, Switzerland; and the fluidized-bed applicator from Chem. Fabrik Stockhausen GmbH).

Turning now to FIG. 1, there is illustrated an absorbent articles of this invention, namely a diaper, which has been assembled from a powder-bonded nonwoven 1 and a liquid-impermeable backing sheet 2, between which is sandwiched an absorbent member in the form of a layer, wad or pad 3. (These components are shown separated in the drawing for reasons of clarity; in practice, however, the nonwoven 1 and the absorbent pad 3 will be in substantial contact, in order to permit the transmission of liquid from the former into the latter.) The powder-bonded nonwoven 1 comprises a first phase 4, in which the fibres are in an unlofted state, and a second phase 5, in which the fibres are in a lofted ("uncompressed" or "bulked") state and which preferably has a higher basis weight than the first phase 4. The said first phase 4 defines an outer surface 6 of the absorbent product. The surface 6 is the one that will be situated against the wearer during use and it is therefore desirable that the said first phase 4 should feel soft and smooth.

The powder-bonded nonwoven material 1 will usually be made of hydrophobic fibres. Furthermore, it is desirable that the material not only should be liquid-permeable but also should enable fast strike-through of liquids to occur. These characteristics permit fluid to pass rapidly into the absorbent pad 3 whilst allowing the nonwoven material 1 to remain substantially dry.

The backing sheet 2 may be formed, for example, of an impervious plastics material; the so-called "breathable" materials can also be used.

The nonwoven 1 and the backing sheet 2 may be held in place relative to the absorbent member 3 by any appropriate means, for example stitching or the use of adhesive material. In another embodiment, the nonwoven material 1 is fastened at its perimeter to the backing sheet 2 to form an envelope containing the absorbent member 3. It is also possible to laminate the absorbent member, if it is of a suitable material and construction (e.g. a tissue), to the nonwoven material; this could render the structure of the product more stable, improve the efficiency of liquid transfer into the absorbent material and result in a product of comparatively thin construction.

The absorbent product may have a size and shape appropriate to the intended use. Other components, e.g. fastening tapes (not shown), may be attached, if required. The use of materials placed intermediate the absorbent member and the nonwoven material is not precluded. For example, the absorbent member may be enclosed by tissue paper or the like. Furthermore, it is possible to employ a nonwoven having, for example, an extra phase situated between the said first and second phases and/or an extra phase at the side of the nonwoven adjacent the absorbent member.

In addition to the elimination of coverstock, the use of the two-(or multi-) phase, powder-bonded nonwoven offers the possibility of further advantages, e.g. whiteness, low linting, dimensional stability and a low content of extractables (polyester bonding powders, for instance, being formaldehyde-free).

The nonwoven material to be used in this invention may be produced by forming, preferably by dry-laying, a layer of fibres that will constitute one of the said first and second phases and depositing thereon, also preferably by dry-laying, a layer of fibres to constitute the other of the said phases. A particulate bonding material is then applied to the resultant layered web and distributed therethrough. The fibrous web is subsequently passed through a heating zone in which the particles are softened or melted, and then through a zone in which it is compressed in order to increase the contact of the molten or softened bonding material with the fibres after which the resultant material is cooled in order to solidify the bonding material and thereby to bond the fibres at points throughout the fibre matrix.

With this method of manufacture, there will be a measure of interpenetration of fibres from the two phases at the junction thereof, this being regarded as an asset in that it helps to preserve the integrity of the nonwoven sheet material during shipping, conversion into the end product and use.

The particles of bonding material applied to the fibrous web may be of any suitable size and shape, for example the rods or granules disclosed, respectively, in U.S. Pat. Nos. 2,880,112 and 2,880,113 to A. H. Drelich. It is preferred to use powdered bonding materials and this invention is therefore described hereinafter with reference to powder-bonded nonwovens.

The technology for producing single-phase powder-bonded nonwovens is known (see, for example, M. F. Meyer, R. L. McConnell and W. A. Haile, "Production of laminates and nonwovens by powder bonding", a paper presented at the INSIGHT '85 Advanced Forming/Bonding Conference, Oct. 27-29, 1985, Toronto, Canada, the teaching of which is incorporated herein by reference). The production of two-phase (or multiphase) powder-bonded nonwovens is analogous and the skilled person should be able readily to produce such nonwovens that are suitable for use in the present invention. By way of illustration, however, the production of a suitable two-phase nonwoven is described below with reference to the production line shown schematically in FIG. 2.

This production line comprises an open-mesh conveyor belt 20 which is driven around the rollers 22, 24 in the direction indicated by the arrow A. One or more textile cards—represented by the single device 26—are provided in order to deposit a layer 28 of fibres on the upper flight of the conveyor belt 20. Another layer 30 of fibres is deposited on top of the layer 28 from one or more further textile cards, represented by the single device 32.

One of the layers constitutes the precursor of the first (unlofted) phase of the nonwoven used in the absorbent product of this invention, whereas the other layer of fibres constitutes the precursor of the said second (lofted) phase. These layers can be deposited in either order. A lofting capability may be achieved by the use of fibres that are crimped; suitable fibres include the crimped polyester fibres, for example such fibres with hollow cross-sections, that are marketed by Eastman Chemical Products Inc. for fibrefill applications.

The two-layer web 34 is passed through a web-spreading section 36 and then to a zone in which the powdered bonding material is applied to the web. This zone is represented by the powder-depositing device 38 (although in practice a plurality of such devices may be used). Suitable powderdepositing devices are powder applicators of the known type in which a wired roller takes powder into the space between the wires and, upon rotation, drops the powder out of that space onto the fibrous web passing beneath it. A screw 40 may be provided in order to raise or lower the roller of the powder-depositing device 38. Furthermore, a receptacle 42 is provided in order to catch any excess powder that falls through the open-mesh belt 20, the powder so collected being available for recycling.

It will be appreciated, of course, that as an alternative to mechanical powder-depositing devices, other applicators such as a fluidising air spray or an electrostatic spray-gun come into consideration, as do devices that apply the powder in a liquid carrier or in the form of a foam.

The bonding powder should have a lower melting point than the fibres in the web; the bonding powder will commonly be of a material having a melting point in the range 80° to 180° C. In general, the bonding powder will be a thermoplastic material and it should be capable of forming a good adhesive bond with the fibres being used. In a number of cases, especially in the case of polyester fibres, a polyester bonding powder will be found to be suitable, for example the polyester powders available from Eastman Chemical Products Inc. as hot-melt adhesives under the trade mark "Eastobond". Typical polyester adhesives have melting points of from 110° to 130° C. and are available as coarse powders (200-420 microns or 70-40 U.S. standard mesh), medium powders (80-200 microns or 200-70 U.S. standard mesh) and fine powders (80 microns or less, or finer than 200 U.S. standard mesh), the medium powders being preferred when using mechanical applicators. Other adhesive binders, for example epoxy resins, also come into consideration. The amount of powder deposited in the web will usually be from 5 to 50% of the total fabric weight, preferably from 10 to 20%.

The two-layer web 34, now with bonding powder distributed through it, is transferred from the conveyor belt 20 to a further conveyor belt 44, for example of Teflon-coated fibreglass, which belt 44 is driven round rollers 46, 48 in the direction indicated by the arrow B and serves to carry the fibrous web 34 through an infrared oven 50. Within the oven 50, the bonding powder fuses and bonds the fibres of the web at points where the fibres and the bonding material come into contact. Upon leaving the oven 50, the web 34 is subjected to light pressure by means of the nip roll 52.

It has been found that the strength of the web material can be improved by reheating. Accordingly, the web 34 leaving the nip roll 52 is transferred to another conveyor belt 54 which is driven round rollers 56, 58 in the direction indicated by the arrow C. As it contacts the conveyor belt 54, the web 34 is carried beneath a water-cooled lightweight roller 60. The web is then carried through a second oven 62 and thereafter is subjected to further compression by means of the nip roll 64. The nip rolls 52 and 64 may be heated during start-up but thereafter cooled during operation. The rollers 46, 48 and 56, 58 may also be water-cooled in order to prevent an excessive build-up of temperature due to the transfer of heat from the oven. The resultant web is then further cooled by passing it around the water-cooled cans 66, 68, following which the web is wound into a roll on the winder 70.

The suitable oven temperatures will depend upon the bonding powder that is used and will be ascertainable from simple trails or from the literature provided by the supplier of the bonding powder. Typically, however, the oven temperatures will be within the range from 80° to 200° C. The temperature of the web emerging from the ovens 50 and 62 may be monitored, for example by means of infrared devices 72 and 74, respectively. It will be appreciated, of course, that the infrared ovens 50, 62 could be replaced by other heating devices, e.g. calenders, hot-air ovens, steam presses and heated contact cans with non-stick surfaces. The dwell time of the web in each oven will depend upon the line speed that is achievable (typically from 50 to 100 metres per minute, although higher speeds may be possible) and other factors, but may typically be from 20 seconds to 2 minutes.

The pressures applied by the nip rolls 52 and 64 will depend upon the materials used, the desired characteristics of the web and the process line conditions; normally, pressures of up to 30 kg, typically up to 20 kg per cm of roll face width are used.

In the powder-bonded, multiphase nonwoven as obtained from the fabric-making line, the thickness of the first phase will be typically from 0.03 to 0.25 mm. The thickness of the loftable phase will be typically from 0.25 to 1.00 mm but upon lofting to form the second phase the increase is typically 5 to 10 times, e.g. 7 times, this thickness.

Clearly, a given volume can contain a greater weight of unlofted material than lofted material and it is therefore preferred, for reasons of economy, to transport and store the sheet material in the unlofted state prior to its conversion to the end absorbent product. In principle, however, the end absorbent product could be manufactured from the nonwoven having a lofted phase as obtained during the above-described process, after cooling as appropriate.

As indicated above, lofting is, in general, effected by the application of heat. Appropriate temperatures and durations of heating may vary according to the nonwoven being treated, but will be readily ascertainable by the skilled person. The lofting mechanism may be explained as follows, with reference to the preferred embodiments described above. As laid, the precursor of the second phase will be thick and of low density owing to the highly crimped form of the fibres that are used. When this web is powdered and compressed (e.g. calendered) in the fabric-making process, the adhesive powder bonds hold down the fibres and constrain them in a flat sheet form. It is in this ("densified" or "compressed") form that the fabric is removed from the fabric-making line. The lofting process occurs when the adhesive powder bonds are softened by heat. The adhesive bonding material melts at a temperature (typically 110° to 130° C.) that is much lower than the melting temperature of the fibres (typically 250° to 290° C.). When heated, therefore, the powder bonds soften and allow the fibres to "regain their memory" and thereby tend to return to the thick, low density form that they were in prior to adhesive bonding. Typically, the lofting temperature will be in the range of 20° to 50° C. above the melting point of the adhesive used. (In general, the fibres of the first phase will have been chosen so that they do not undergo lofting during this heating step, whereby the first phase may retain a surface that is comfortable to the touch.) The lofted material then cools in its lofted state and the adhesive resets and thereby stabilises the second phase in its lofted form.

It will be appreciated by the skilled reader that the absorbent articles of the present invention could be used outside the field of disposable personal hygiene aids. For instance, the products may be used in the medical field, as bandaging or as wound dressings (subject to approval by the appropriate regulatory body).

It will be course be understood that the present invention has been described above purely by way of example, and modifications of detail can be made within the scope of the invention.

I claim:

1. An absorbent product comprising an absorbent member at least part of which is overlaid with a sheet of particle-bonded nonwoven material having a first phase that is in an unlofted state and a second phase that is in a lofted state and that has been formed by the heat treatment of a precursor phase comprising crimped fibers, the second phase being between the first phase and the absorbent member.

2. An absorbent product according to claim 1 in which the absorbent member comprises comminuted cellulose fibers, a super-absorbent polymer, or a mixture thereof.

3. An absorbent product according to claim 1 in which the said first phase has a basis weight of from about 10 to about 50 g/m$^2$.

4. An absorbent product according to claim 3 in which the said second phase has a basis weight of from about 30 to about 80 g/m$^2$.

5. An absorbent product according to claim 1 in which the nonwoven material comprises polyester fibers.

6. An absorbent product according to claim 1 in which the fibres within the nonwoven material are bonded with a polyester.

7. An absorbent product according to claim 5 in which the fibers within the nonwoven material are bonded with a polyester.

8. An absorbent product according to any one of claims 1 or 2 to 7, inclusive, in the form of a baby's diaper, an adult's incontinence pad or a lady's sanitary napkin.

9. An absorbent product according to claim 1 in which the nonwoven material is made of hydrophobic fibers.

10. An absorbent product according to claim 1 in which the particle-bonded nonwoven material is a powder-bonded nonwoven material.

11. An absorbent product according to anyone of claims 1, 2 or 9 in which the absorbent member is sandwiched between the sheet of particle-bonded nonwoven material and a liquid-impermeable backing sheet.

* * * * *

UNITED STATES PATENT AND TRADEMARK OFFICE
CERTIFICATE OF CORRECTION

PATENT NO. : 4,857,065

DATED : August 15, 1989

INVENTOR(S) : Michael J. Seal

It is certified that error appears in the above-identified patent and that said Letters Patent is hereby corrected as shown below:

Title Page, " [22] Filed: Aug. 15, 1989" should read
-- [22] Filed: Nov. 18, 1987 --.

Column 4, Line 27, "powderdepositing" should read
-- powder-depositing --.

Column 4, Line 36, "recycyling" should read -- recycling --.

Column 5, Line 27, "trails" should read -- trials --.

Column 6, Line 32, "be" (first occurrence) should read -- of --.

Signed and Sealed this

Ninth Day of April, 1991

*Attest:*

HARRY F. MANBECK, JR.

*Attesting Officer*      *Commissioner of Patents and Trademarks*